(12) United States Patent
Diano et al.

(10) Patent No.: US 6,556,698 B1
(45) Date of Patent: Apr. 29, 2003

(54) METHOD AND SYSTEM FOR ASSOCIATING EXPOSED RADIOGRAPHIC FILMS WITH PROPER PATIENT INFORMATION

(75) Inventors: Francesco Diano, Vado Ligure (IT); Giovanni Venturi, Genoa (IT)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/294,503

(22) Filed: Apr. 20, 1999

(30) Foreign Application Priority Data

Apr. 24, 1998 (EP) .............................. 98107487

(51) Int. Cl.[7] ................................................ G06K 9/00
(52) U.S. Cl. .............. 382/132; 250/370.09; 250/390.02
(58) Field of Search ................................. 382/128, 129, 382/131, 132, 130, 282, 284, 298; 358/457; 378/28, 46, 90, 92, 140, 165, 166; 250/370.09, 390.02

(56) References Cited

U.S. PATENT DOCUMENTS

| | | | |
|---|---|---|---|
| 5,172,419 A | * | 12/1992 | Manian ...................... 382/132 |
| 5,237,358 A | | 8/1993 | Yamada et al. |
| 5,384,862 A | * | 1/1995 | Echerer et al. .............. 382/132 |
| 5,583,663 A | | 12/1996 | Boeve |
| 5,694,450 A | | 12/1997 | Livingston |
| 5,740,267 A | * | 4/1998 | Echerer et al. .............. 382/132 |
| 5,917,929 A | * | 6/1999 | Marshall et al. ............. 382/128 |
| 6,198,837 B1 | * | 3/2001 | Sasano et al. ................ 382/132 |

FOREIGN PATENT DOCUMENTS

| | | |
|---|---|---|
| EP | 0414042 A2 | 8/1990 |
| EP | 0 452 570 A1 | 10/1991 |

* cited by examiner

*Primary Examiner*—Timothy M. Johnson
*Assistant Examiner*—Abolfazl Tabatabai
(74) *Attorney, Agent, or Firm*—William F. Noval (57) ABSTRACT

A method and system is described which facilitates the proper association of radiographic film with a patient information. The invention maintains information for each patient to be examined in the current day and generates a unique identifying ID code for each patient to be examined. Before examining a patient, the current patient's unique identifier is imaged on an unexposed radiographic film. After the patient is examined and the film is exposed, the film is developed and digitized. Patient information is retrieved and associated with the digitized medical images by analyzing the digital image data in order to determine the patient's unique identifier. In this manner, the invention ensures the proper association of patient information with exposed radiographic film. Once properly associated, the digital image data and the patient information can be communicated to a Picture Archiving and Communication System. The present invention also allows for interfacing with a hospital's Radiology Information System, thus eliminating the need for manual entry of patient information.

22 Claims, 9 Drawing Sheets

METHOD AND SYSTEM FOR ASSOCIATING EXPOSED RADIOGRAPHIC FILMS WITH PROPER PATIENT INFORMATION

FIELD OF THE INVENTION

This invention relates generally to the field of medical imaging, and more particularly to a method and system for associating exposed radiographic films with proper patient information.

BACKGROUND

Many modern hospitals have implemented a variety of digital medical modalities such as a magnetic resonance (MR), computed tomography (CT), digital radiography, and ultrasound devices. These modalities, often referred to as input imaging devices, produce vast numbers of diagnostic quality digital images. In order to handle the large volume of digital images, many hospitals have implemented networks of specialized equipment and components specifically designed to facilitate medical radiological imaging. Such a network is commonly referred to as a Picture Archiving and Communicating System (PACS). A PACS allows a radiologist to easily manage digital medical images including storing, retrieving, and viewing the images. For example, when a patient is imaged by a medical modality, a series of digital images, often referred to as a "study", is generated and archived at a central database. Typically each study contains general patient information such as name, date of birth, an assigned physician and the type of medical modality that produced the images. This information is often entered by hospital personnel from a workstation while the patient is being imaged. After imaging is complete, a radiologist can easily retrieve the patient's study from the database and print the images on a medical imager.

A medical imager processes the pixel data of the retrieved medical images and generates output image data. For example, in a continuous tone laser imager, the output image data represents exposure levels necessary for a scanning assembly to accurately reproduce the original image on an imaging element. The output image data is used to modulate the intensity of the scanning laser while exposing the imaging media, thereby forming the visible representation of the original image. Other medical imagers use different imaging techniques to form output images such as direct thermal imaging, ablation imaging, dye transfer, ink jet, dye sublimation and thermal mass transfer.

In addition to easily printing stored medical images, a PACS allows a radiologist to view each image on a diagnostic-quality display station. This eliminates any expense and effort involved in printing the images. Furthermore, after viewing the images, the radiologists can forward the study to another radiologist, perhaps located at a remote hospital, for further review. In this fashion, PACS have greatly improved patient care and the efficiency of radiology departments.

One area that has not benefited from the recent progress in managing and archiving images is conventional radiography (X-ray). In conventional radiography, a radiographic film captures an image-wise exposure of a patient. The exposed film is then chemically developed to form a visible image. Because of the high image quality, conventional radiography is still the predominant diagnostic technique employed by radiologists. Unfortunately, because of the exposure and development process, conventional radiography has been unable to enjoy the benefits associated with digital imaging described above. Many hospitals have attempted to address this problem by turning to film digitizers which digitize radiographic images formed on radiographic films. Once the radiographic image is available in digitized form, such an image can be archived, retrieved and manipulated in any of the various ways offered by a PACS. For this purpose, the developed film is manually removed from the developer and fed into the film digitizer. This approach, although producing a digital image, requires vast amounts of time and labor. Furthermore, manual operations are required in order to associate each digitized image to the proper patient and the communication of the complete study to the PACS. Such a manual operation requires a high degree of attention and is prone to error. For example, patient information is often associated with the wrong image. Another attempt to solve the above problem, as discussed in U.S. Pat. Nos. 5,237,358, 5,583,663 and EP 452,570, has been to directly couple the film processor to the film digitizer such that developed film is fed directly into the film digitizer. This technique requires less time and manual labor and offers other benefits including reducing the chance the film is blemished with finger marks, dust, or the like. This technique, however, does not address the problem that the generated images must be associated with the proper patient information.

By facilitating the management of digital medical images, PACS have greatly improved patient care and the efficiency of radiology departments. For the reasons stated above, and for other reasons stated below which will become apparent to those skilled in the art upon reading and understanding the present specification, there is a need in the art for a method and system which facilitate the use of conventional radiographic film in a PACS environment. There is also a need for a method and system which automatically associates medical images from exposed radiographic film to correct patient information.

SUMMARY OF THE INVENTION

The present invention is directed to a method and system for automatically associating a radiographic film with one of a plurality of patients. In one embodiment, the present invention generates a unique code for each patient that is scheduled for examination. When a particular patient is to be examined, the patient's corresponding unique code is imaged on an unexposed radiographic film. The patient's image is captured on the radiographic film which is then developed to form at least one visible medical image on the radiographic film. The developed radiographic film is digitized to produce digital image data. According to the present invention, the digital image data is analyzed to determine the unique code of the examined patient that was imaged on the film. The proper patient information is associated with the developed radiographic film based on the unique code as determined from the digital data. According to one aspect of the present invention, the digital image data is analyzed according to optical character recognition techniques.

According to yet another aspect, the present invention stores patient information in an information table having a plurality of entries such that each entry of the information table can be accessed by one the unique identifiers. After a radiographic film is digitized, the information table is accessed according to the unique identifier determined from the digital image data in order to retrieve proper patient information. In one embodiment, the present invention retrieves current patient information from a radiology information system.

According to one feature, the present invention retrieves the proper patient information and communicates the digital image data and the retrieved patient information to a Picture Archiving and Communicating System. In one embodiment, the digital image data and the retrieved patient information is communicated in compliance with the DICOM standard, such as by constructing a DICOM file.

According to yet another aspect, the present invention provides a visual display to allow an operator to modify the patient information of the information table. For example, an error message is displayed when the present invention is unable to determine the unique patient identifier from the digital image data. Providing a visual display allows the operator to enter patient information for the developed radiographic film.

In another embodiment, the present invention is a system for associating a radiographic film with one of a plurality of patients. The system includes an imager for imaging a label having a unique patient identifier on radiographic film. The system further includes an input imaging device having a processor for developing the radiographic film with the label imaged thereon, thereby forming at least one visible medical image on the radiographic film. A film digitizer is coupled to the processor for digitizing the medical image and the label image, thereby producing digital image data. An interface device receives the digital image data and analyzes the digital image data in order to correctly associate the developed radiographic film with one of the patients. According to one aspect of this embodiment, the interface device stores patient information in an information table having a plurality of entries such that each entry of the information table has a unique identifier. The interface device selects one of the entries of information table when the entry's unique identifier corresponds to the unique patient identifier of the label as determined from the digital image data.

According to one aspect of this embodiment, the interface device further comprises (i) a patient identification station for managing the information table including retrieving patient information from the selected entry, and (ii) a network interface for receiving the digital image data from the input imaging device and communicating the patient identifier to the patient identification station. According to another aspect of this embodiment, the network interface includes a DICOM manager for building a DICOM file containing the digital image data and the patient information received from the patient identification system, wherein the network interface communicates the DICOM file to a Picture Archiving and Communicating System. These and other features and advantages of the invention will become apparent from the following description of the preferred embodiments of the invention.

DETAILED DESCRIPTION

Figure 1:
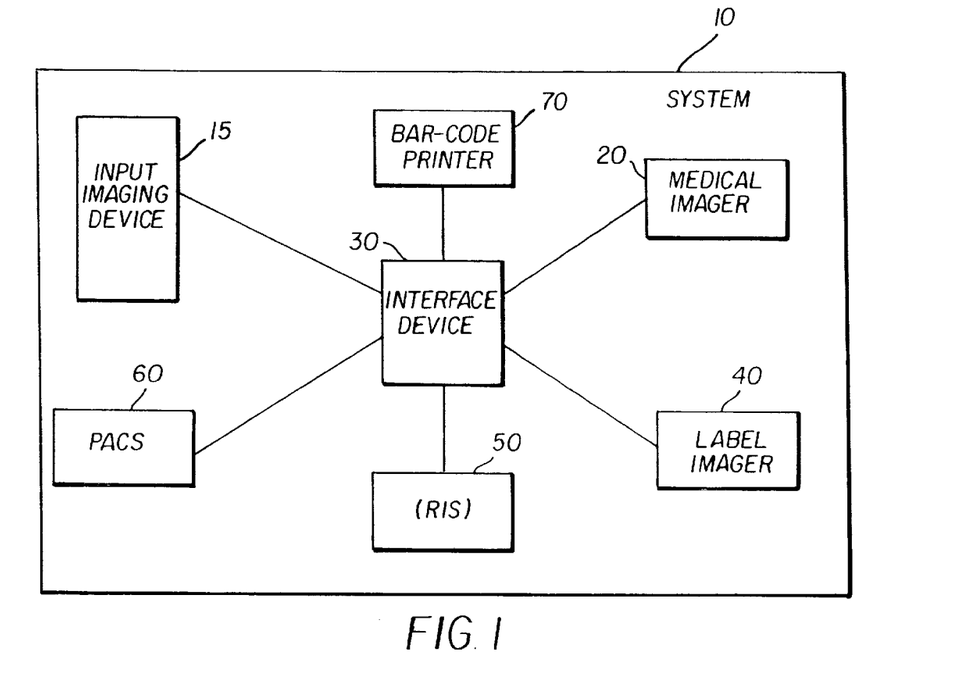
FIG. 1 is a block diagram of one embodiment of a medical image management system having an interface device for associating radiographic film to proper patient information in accordance with the present invention.

FIG. 1 illustrates one embodiment of a medical image management system 10 in block diagram form. System 10 includes input imaging device 15, medical imager 20, interface device 30, label imager 40, Radiology Information System (RIS) 50, PACS 60, and bar-code printer 70. Input imaging device 15 produces digital images and communicates the images to interface device 30. For example, in one embodiment input imaging device 15 includes a processor for developing conventional radiographic film, such as film exposed via conventional X-ray, and a digitizer coupled to the processor for receiving the developed film and generating digital image data by digitizing the radiographic film. In one preferred embodiment, input imaging device 15 comprises the apparatus described in EP Application No. 97-120678.4 filed on Nov. 26, 1997 and titled "Apparatus for Processing And Digitizing A Radiographic Film," the description of which is herein incorporated for reference.

As will be described in detail below, interface device 30 maintains information of patients scheduled to be examined and control label imager 40 such that a unique patient identifier is imaged on each radiographic film used for examining the scheduled patients. After input imaging device 15 develops and digitizes a radiographic film, interface 30 receives the generated medical images in the form of digital image data and automatically associates each of the images with the correct patient information by examining the digital image data and determining the unique patient identifier. After associating the proper patient information with each image, interface device 30 communicates the digital image data and the proper patient information to PACS 60. In one embodiment, interface device 30 communicates the medical images and the associated patient information to PACS 60 using a data communications protocol developed by the American College of Radiology (ACR) and the National Electrical Manufacturers Association (NEMA) known as the DICOM protocol. The DICOM protocol is typically implemented using a TCP/IP connection between the communicating devices. By automatically associating images generated by input imaging device 15 with proper patient information, interface device 30 eliminates the vast amounts of time and labor required to enter patient information and ensure the association of the information with the appropriate images.

In addition to communicating received images to PACS 60, interface device 30 may communicate the images to medical imager 20 which is any medical imager suitable for forming a representative output image on an imaging element. Typically, input imaging device 15 communicates the input pixel data of the input image as well as imaging commands that specify operations to be performed by medical imager 20 on the communicated input pixel data such as image rotation or polarity reversal. In one embodiment, medical imager 20 is a continuous tone laser imager. Furthermore, the imaging element may be photographic such that medical imager 20 includes a processor station (not shown) for chemical processing and developing of the output image formed on the imaging element. In another embodiment, the imaging element is photothermographic which can be thermally processed and need not be chemically processed.

Figure 2:
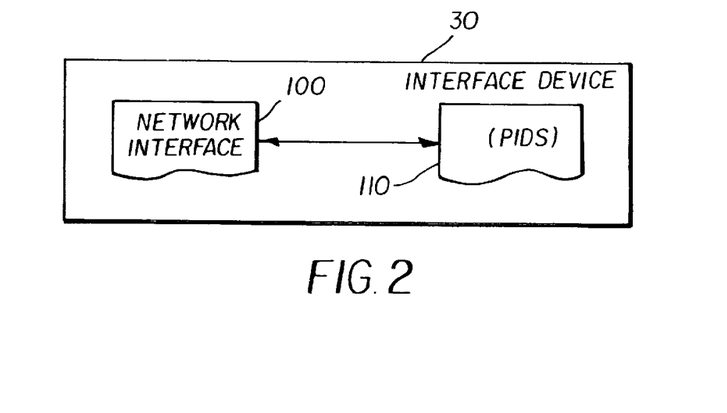
FIG. 2 is a block diagram of one embodiment of the interface device having a network interface and a patient ID station.

FIG. 2 illustrates one embodiment of interface device 30 having a network interface 100 and a patient ID station (PIDS) 110. In addition to receiving the digital images from input imaging device 15, network interface 100 is responsible for all communications with PACS 60 including, in one embodiment, the construction of appropriate DICOM messages and the communication of these messages. PIDS 110 is mainly devoted to associating the received images with the proper patient information, communicating with label imager 40 and medical imager 20 and providing a user with a visual interface for operating and configuring interface device 30. More specifically, PIDS 110 maintains information for each patient scheduled to be examined and generates a unique identifier for each patient. As will be detailed below, PIDS 110 ensures that unexposed radiographic film is labeled with one of the unique identifiers corresponding to the current patient being examined. Network interface 100 is responsible for receiving the digital image data from input imaging device 15 and analyzing the image data to determine the unique identifier imaged on the digitized radiographic film. Based on the determined unique identifier, PIDS 110 communicates the proper patient information to network interface 100. In this manner, network interface 100 and PIDS 110 ensure the proper association of patient information to digitized radiographic film. In one embodiment, network interface 100 and PIDS 110 execute on a single computer. In another embodiment, network interface 100 and PIDS 110 execute on two separate computers such that network interface 100 executes on a computer without a monitor or a keyboard and depends on PIDS 110 for visual and administrative tasks.

Figure 3:
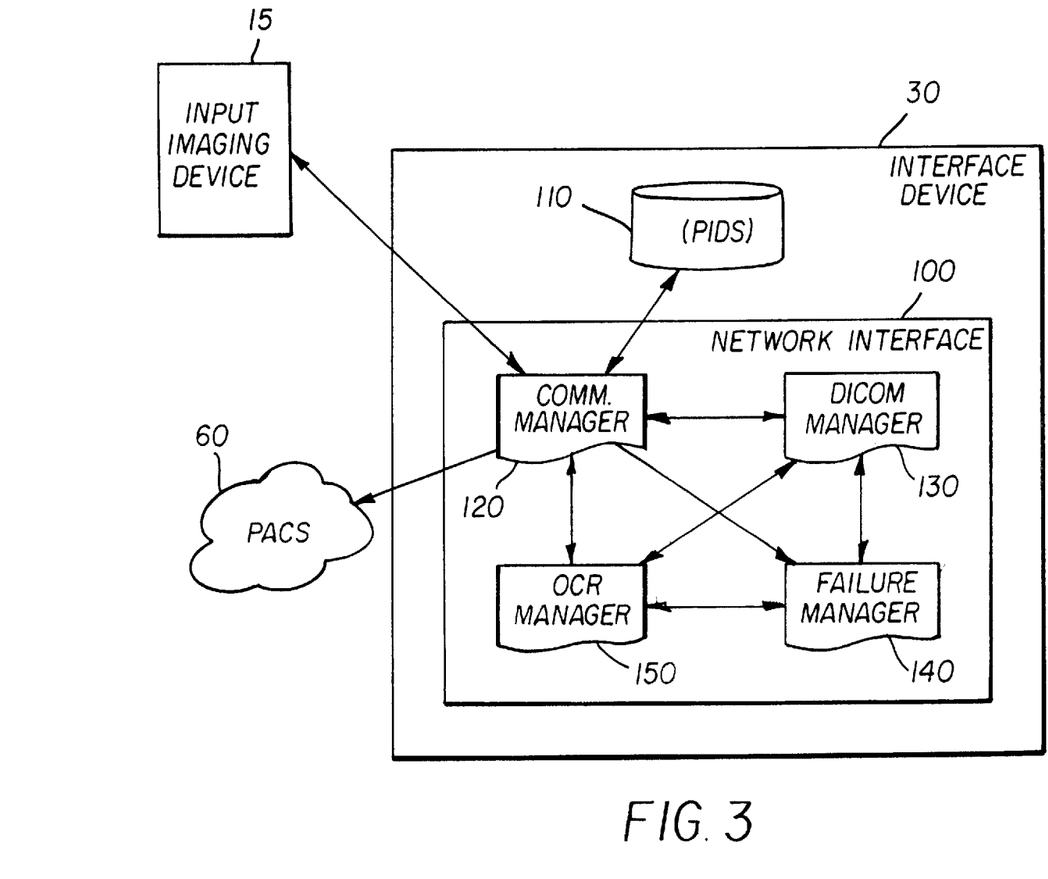
FIG. 3 is a block diagram of one embodiment of the network interface.

FIG. 3 illustrates in detail one embodiment of network interface 100 having communication manager 120, OCR manager 150, DICOM manager 130 and failure manager 140. In this embodiment, communication manager 120 manages all communications of the network interface 100 with the other components including input image device 15, PIDS 110 and PACS 60. OCR manager 150 processes each digital image received from input imaging device 15 according to character recognition methods in order to determine patient identification data recorded in the image data. In one embodiment, OCR manager 150 extracts a patient ID code and other general information of the patient which was imaged as a label on the digitized X-ray film. DICOM manager 130 constructs any DICOM data structures, such as messages or files, that are necessary for communicating image and patient information to PACS 60. Failure manager 140 handles any errors that may occur within interface device 30 such as OCR failure or communication failure. OCR failure is handled by storing the failed image and requesting operator intervention by sending an OCR failure message to the PIDS through the communication manager 120. Communication failure is managed by storing the image and periodically retrying the communications. In one embodiment, network interface 100 of interface device 30 is directly connected to input imaging device 15 via a fast Ethernet link, to PIDS 110 with a LAN link, and to PACS 60 with a LAN link.

Figure 4:
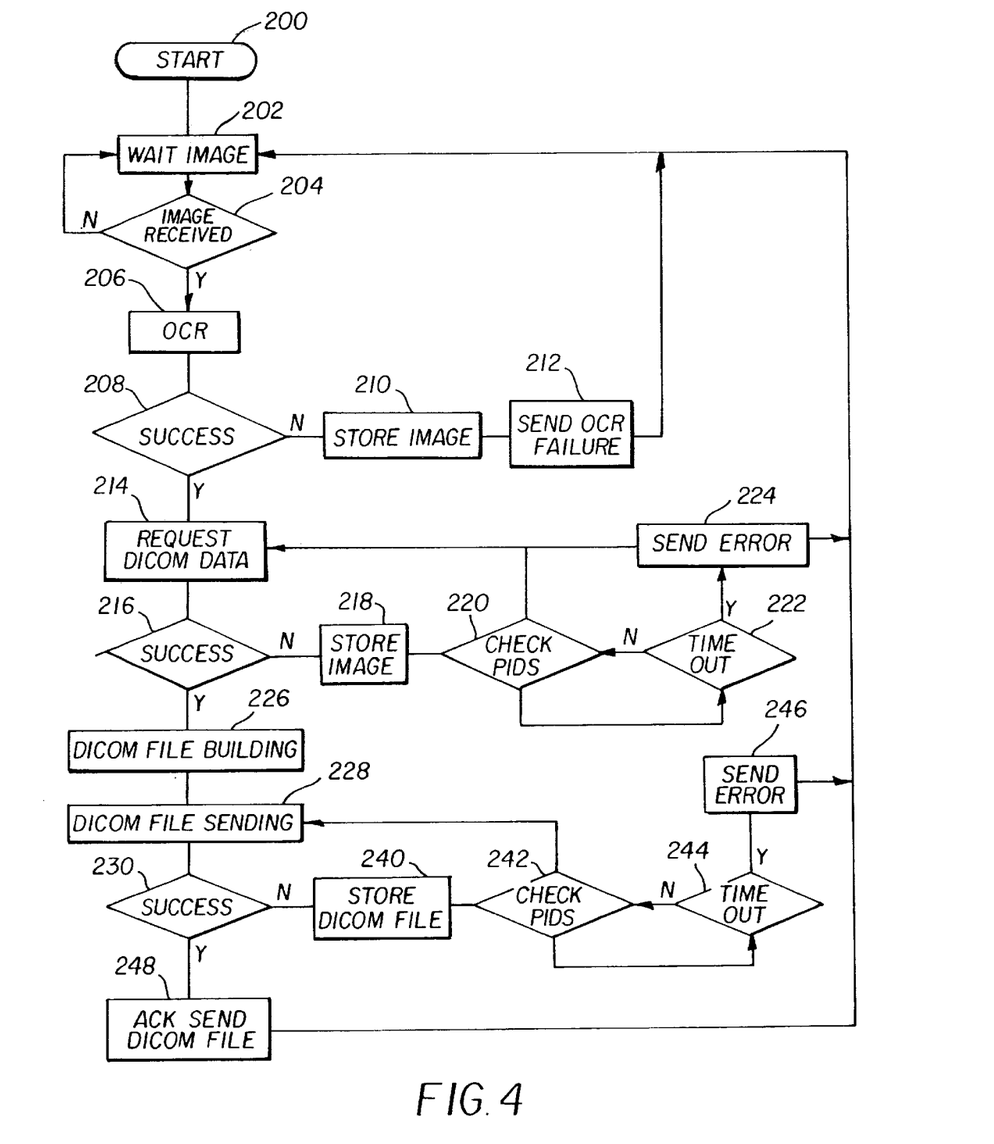
FIG. 4 is a flowchart illustrating one mode operation of network interface.

FIG. 4 is a flow chart illustrating one mode of operation of the network interface 100. Network interface 100 begins execution in step 200 and immediately proceeds to step 202 where communication manager 120 waits for digital image data from input imaging device 15. When a new image is received, communication manager 120 proceeds from step 204 to step 206 and communicates the received image to OCR manager 150. OCR manager 150 performs character recognition operations on the image data in order to determine a patient identifier, such as an ID code, stored in the image data received from communication manager 120. If OCR manager 150 is unable to retrieve a valid patient ID code, failure manager 140 stores the corresponding image in step 210 and sends an OCR failure message to the operator through PIDS 110. In one embodiment, failure manager 140 stores the failed image in a specific directory of a hard disk embedded within network interface 100. After failure manager 140 handles the OCR failure, network interface 110 returns to step 202 and waits for subsequent images.

If OCR manager 150 is able to extract the patient identifier from the received image data, OCR manager 150 communicates the extracted patient identifier to communication manager 120. In step 214, communication manager 120 communicates the patient identifier to PIDS 110 and requests full patient information such as patient and study data, general equipment data and secondary equipment data. In one embodiment, communication manager 120 requests PIDS 110 to format the information so as to comply with the DICOM standard. In step 216, communication manager 120 determines whether the request for patient information is successful. If the request does not succeed, the image is stored by means of the failure manager 140 in step 218 and communication manager 120 polls PIDS 110 until success occurs in step 216 or a timeout expires in step 222. If time-out occurs, failure manager 140 sends an error message to the operator through PIDS 110. After failure manager 140 sends the error message, network interface 110 returns to step 202 and waits for subsequent images.

If the request for patient information succeeds in step 216, network interface 100 proceeds to step 226 where communication manager 120 communicates the patient information to DICOM manager 130. DICOM manager 130 receives the patient information and builds a DICOM file by combining, according to the DICOM standard, the image data and the data received from PIDS 110. DICOM manager 130 communicates the constructed DICOM file, or at least a pointer to the DICOM file such as a filename, to communication manager 120.

In step 228, communication manager 120 transmits the DICOM file to PACS 60. If a communication failure occurs while sending the DICIOM file, failure manager stores the DICOM file in step 240 and communication manager 120 waits for a success response from PACS 242 in step 242 until a second predetermined timeout expires in step 222. If time-out occurs, failure manager 140 sends an error message to the operator through PIDS 110. After failure manager 140 sends the error message, network interface 110 returns to step 202 and waits for subsequent images. If the constructed DICOM file is successfully communicated, communication manager 120 sends an acknowledgment message to PIDS 110. Network interface 100 proceeds from step 248 to step 200 and waits for subsequent medical images from input imaging device 15.

Figure 5:
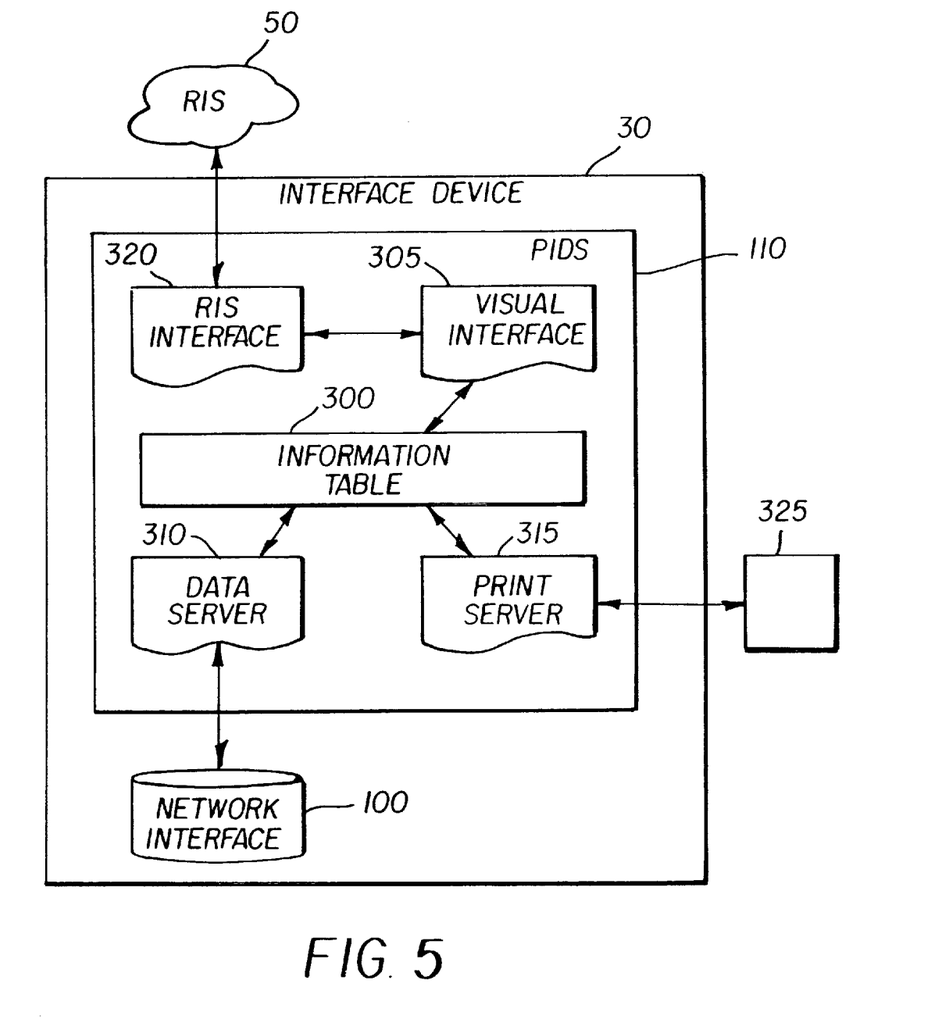
FIG. 5 is a block diagram of one embodiment of the patient ID station.

FIG. 5 illustrates one embodiment of PIDS 110 having information table 300, visual interface 305, data server 310, print server 315 and Radiology Information System (RIS) interface 320. Information table 300 contains information necessary to correctly associate patient information received from RIS 50 with digital image data received by network interface 100 from input imaging device 15. Visual interface 305 provides a visual display and input interface to the operator of interface device 30. Data server 310 manages client/server communication and data transfer between network interface 100 (the client) and PIDS 110 (the server). Print server 315 is the server component of a client/server interface to label imager 40 (the client). RIS interface 320 is the client component of a client/server interface between PIDS 110 and RIS 50 (the server). Each of these components of PIDS 110 is discussed below.

Information Table

PIDS 110 maintains information table 300 which defines all information necessary to form a message, or file, for communicating with PACS 60. In one embodiment, information table 300 includes a set of databases and/or tables of the information needed to construct a DICOM file according to the DICOM standard. In general, the DICOM standard provides standardized format for images, a common information model, application service definitions, and a protocol for communication. Therefore, in this embodiment, the information stored in the information table 300 includes: (1) Patient's and Study Data, (2) General Equipment Data, and (3) Secondary Equipment Data, and are preferably stored in three different files (PSD file, GED file and SED file, respectively). The information regarding patient's and study data is specific for each patient. The PSD file is configured as a list of records where each record corresponds to a patient. The following table lists the various fields of a record in the PSD file:

TABLE 1

| Field | Data Structure (1 char = 1 byte) |
|---|---|
| Patient Name | Char [64] |
| Patient ID | Char [64] |
| Patient Birth Date | Char [8] (Fixed yyyymmdd) |
| Patient's Sex | Char [16] |
| Other Patient ID | Char [64] |
| Study ID | Char [16] |
| Study Date | Char [8] (Fixed yyyymmdd) |
| Study Time | Char [16] (Fixed hhmms.frac) |
| Referring Physician Name | Char [64] |
| Study Description | Char [64] |
| Admitting Diagnosis Description | Char [64] |
| Accession Number | Char [16] |
| Series Number | Char [12] |
| Body Part Examined | Char [16] |
| Laterality | Char [16] |
| Patient Orientation | Char [16] |
| Unique (Axdis) Code | Char [5] Fixed |

Each of the above listed fields is divided in other two sub-fields. The first sub-field contains the field identifier for the data according to the DICOM standard. The second contains a corresponding DICOM field value. For instance, the Patient Name field contains the patient name and a predefined value, such as 00100010, which is defined by the DICOM standard.

The General Equipment Data describes the medical modality used for primary capture and the institution and department name of the organization that is performing the exam. This information is usually common for each patient and is changed infrequently. The following table describes one embodiment of the GED file:

TABLE 2

| Field | Data Structure | Data Identifier |
|---|---|---|
| Manufacturer | Char [64] | 0008,0070 |
| Manufacturer's Model Name | Char [64] | 0008,1090 |
| Institution Name | Char [64] | 0008,0080 |
| Institution Dept. Name | Char [64] | 0008,0050 |

The Secondary Equipment Data is common for every patient and is rarely changed. The structure of the SED file consists in a unique record which contains 7 fields as required by the DICOM standard. It lists the values required from the DICOM standard for a secondary capture device which, according to the present invention, is a film digitizer within input imaging device 15. The following table describes the fields of the SED file with the corresponding data structure and DICOM data identifier:

TABLE 3

| Record | Data Structure | Data Identifier |
|---|---|---|
| Conversion Type | Char [16] | 0008,0064 |
| Modality | Char [16] | 0008,0060 |
| SC Device ID | Char [64] | 0018,1010 |
| SC Device Manufacturer | Char [64] | 0018,1016 |
| SC Device Manufacturer's Model Name | Char [64] | 0018,1018 |
| SC Device Software Version | Char [64] | 0018,1019 |
| Digital Image Format Acquired | Char [64] | 0018,1023 |

Information table 300 further includes Process Information which includes information relating imaging a label having the patient identifier on a radiographic film. Preferably, this information is stored in a file referred to as the ID ACK file. The Process Information further includes information relating to the notification that a DICOM file has been successfully sent to PACS. Preferably, this information is stored in a file referred to as the PACS ACK file.

Visual Interface

As mentioned above, visual interface 305 provides a visual display to the operator of interface device 30 and allows the operator to create, store and edit current patient information. Thus, visual interface 305 main function consists in the creation and updating of the PSD file containing all the patient and study data associated with a patient identifier, such as an ID code. Visual interface 305 receives a manually entered patient list from the operator or, in another embodiment, retrieves a patient list from RIS interface 320. More specifically, via visual interface 305, the operator may easily build the list of patients who have been scheduled for a particular day. The operator enters the patient data, the day of the examination and other additional information. Alternatively, the patient information is retrieved from the RIS 50 via RIS interface 320 by means of a client/server process. Visual interface 305 generates the above described PSD file based on the received patient list and stores the generated PSD file in information table 300. In this manner, visual interface may be used within a hospital environment where no RIS/HIS system is present or in hospitals already equipped with a RIS/HIS.

In addition to facilitating the creation and maintenance of a current patient list, visual interface 305 provides warning messages in case of failure of various components/modules of the system of the present invention. For example, visual interface 305 allows the operator to view the status of all the devices present in the system. The operator may obtain a summary about the status of all the device present in the system by accessing to a file resident in network interface 100. Under request, visual interface 305 creates a status window and displays the status of each devices.

Visual interface 305 also allows the operator to view images that generated an OCR failure and to associate the failed images to the proper patient information in the patient database. The operator may view these images by using a particular command of visual interface 305. When the image is shown, the operator can enter the patient name and/or the ID code corresponding to the failed image. The entered information is communicated from visual interface 305 to network interface 100.

Visual interface 305 also allows the operator to view an overview status of each patient, such as, for example, label imaged (when receiving the label imaged acknowledgment from the label imager, print server 315 sets as done the Label Imaged field of the ID ACK file), exams executed (when receiving the request of patient data from network interface, the data server sets as done the Exam Developed field of the PACS ACK file), exams sent to the PACS (when receiving the acknowledgment flag from network interface, the data server sets as done the Image Sent field of the PACS ACK file), and so on.

Figure 6:
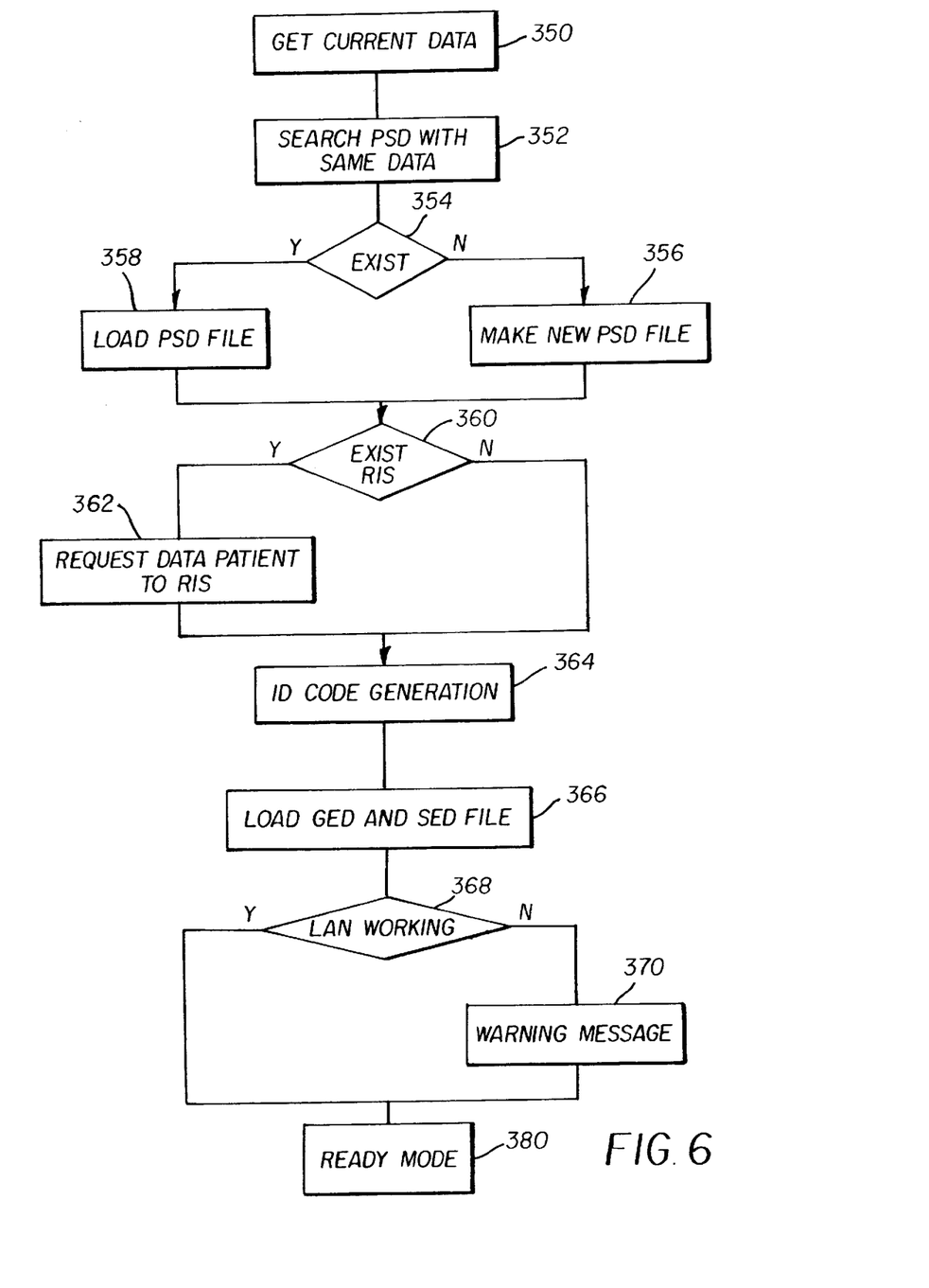
FIG. 6 is a flowchart for illustrating one mode of operation of a visual interface for the patient ID station.

FIG. 6 is a flow chart illustrating one mode of operation of visual interface 305. Visual interface 305 begins execution at step 350 by retrieving the current date. In steps 352 and 354, visual interface 305 determines whether a PSD file corresponding to the current date exists within information table 300. If this file is not found, visual interface 305 proceeds to step 356 and creates the PSD file according to the current date. If the file is found, visual interface 305 proceeds to step 358 and retrieves the data stored in the PSD file. Visual interface 305 then proceeds to step 360 and checks for the presence of RIS interface 320. If RIS interface 320 is detected, visual interface 305 proceeds to step 362 and sends RIS interface 320 a request for a daily patient list. When visual interface 305 receives the list, it updates the PSD file. Visual interface 305 proceeds from steps 360 and 362 to step 364 and generates a unique patient identifier, such as an ID code, for each patient present in the PSD file. In one embodiment, visual interface 305 generates a five digit ID code according to the current date such that the ID code. The first two digits identify the day of the current date and are comprised between 1 and 31. The last three digits identify an entry within the PSD file and are comprised between 0 and 999. Upon generating the patient identifier, visual interface 305 proceeds to step 368 and loads the GED and SED files and checks for the LAN connection with network interface 100. If the LAN connection is not working, visual interface 305 provides a warning message to the operator in step 370 and proceeds to step 380 and enters in a ready mode in which visual interface 305 waits for messages from the operator or from the other modules of the system.

Figure 7:
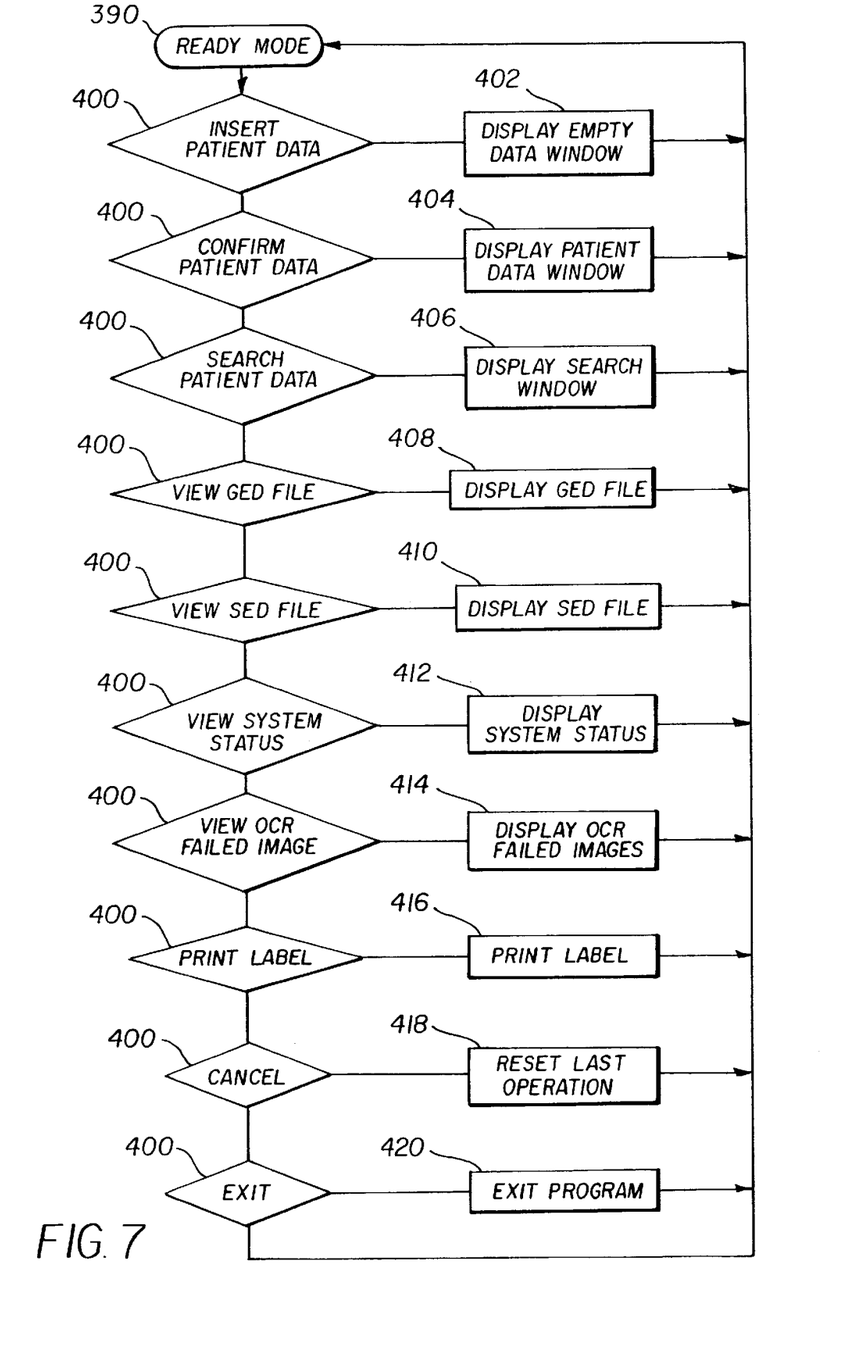
FIG. 7 is a flowchart for illustrating various operations that may be performed by hospital personnel via the visual interface.

FIG. 7 illustrates a plurality of operations that the operator can perform via visual interface 305. When visual interface 305 receives an operator request, it proceeds through a series of tests, indicated as steps 400, to determine the operation selected by the operator. Upon determining the operation, visual interface 305 proceeds to the corresponding step and executes the selected operation. Each operation is discussed below.

1. Insert new patient data—step 402: the operator can add a patient, and the corresponding data, to the daily patient list. Visual interface creates an empty data window ready to accept new data. After insertion of the new data, visual interface 305 updates the PSD file and generates an ID code corresponding to the new patient.

2. Confirm patient data—step 404: visual interface 305 confirms that the data of a patient is correct. Visual interface 305 displays all the patient data and checks the values according to the DICOM standard. If a mistake occurs, a warning window appears to warn the operator to correct the wrong value. After correction, visual interface 305 updates the PSD file with the correct values.

3. Search patient data—step 406: allows the operator to quickly check if a patient is present in the PSD file.

4. List general equipment—step 408: allows the operator to view and/or modify the data contained in the GED file of information table 300.

5. List secondary equipment—step 410: allows the operator to view and change the data contained in the SED file of information table 300.

6. View system status—step 412: allows the operator to view the current status of all the devices present in the system.

7. View OCR failed images—step 414: allows the operator to view the images not recognized by the OCR module in the network interface 100 and to insert the ID code or the patient name corresponding to the image shown.

8. Print label—step 416: allows the operator to print a label containing a unique patient identifier and the main generalities of the patient. This option is only available when the system comprises the bar-code printer 70. This command allows to print general patient information and a bar-code on a patient card or sheet.

9. Cancel button—step 418: allows the operator to delete the last operation performed.

10. Exit button—step 420: allows the operator to exit from the program. Visual interface 305 saves all introduced data into the corresponding files.

Data Server

Referring again to FIG. 5, data server 310 manages all communication and data transfer between network interface 100 and PIDS 110. Data server 310 receives the client requests from communication manager 120 of network interface 100 for patient information corresponding to a patient identifier. In response to the request, data server 310 retrieves patient information from information table 300 and communicates the information to communication manager 120 of network interface 100. In addition, data server 310 receives the failure messages coming from the communication manager 120 and forwards them to visual interface 305 which displays a warning to the operator.

Figure 8:
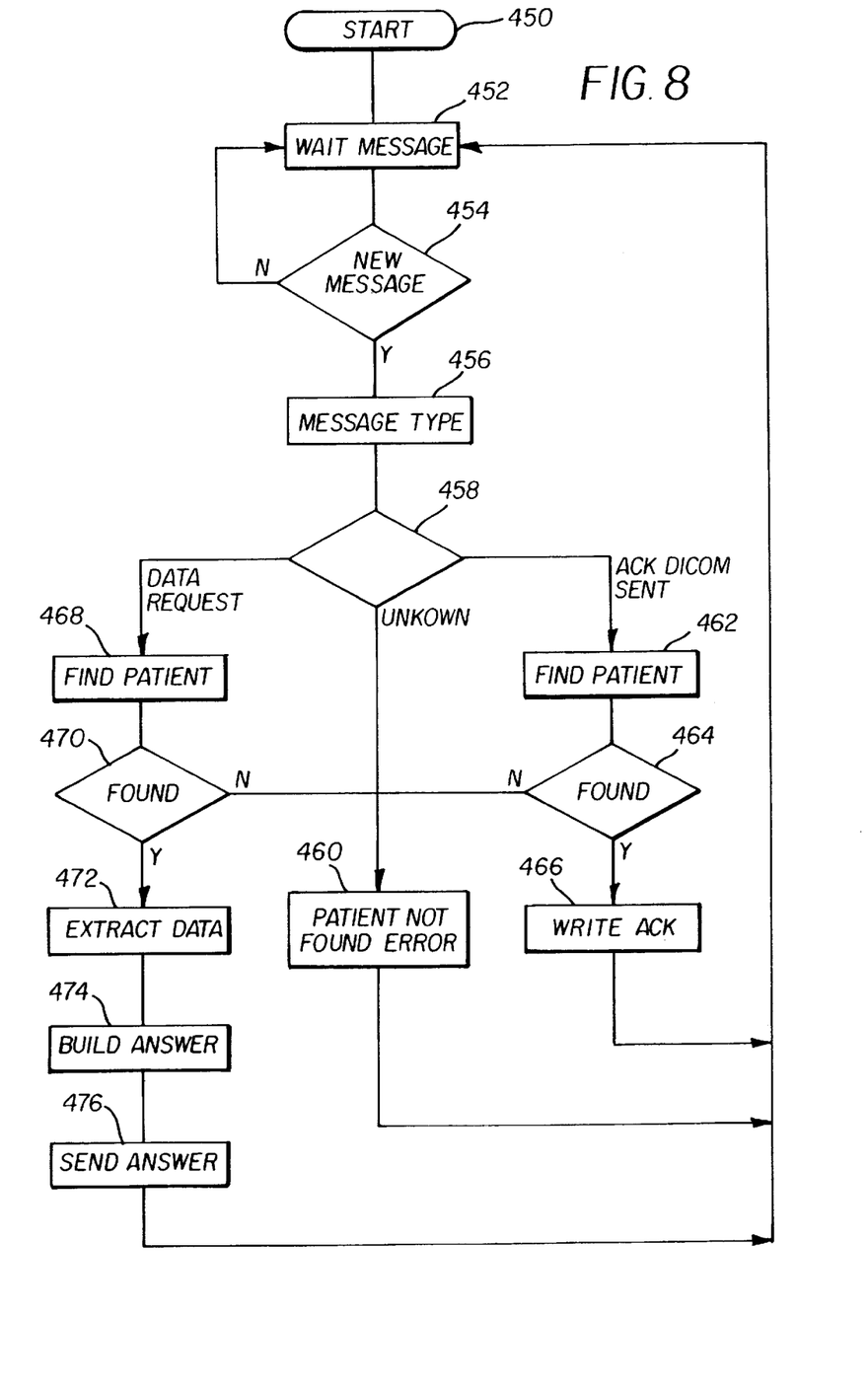
FIG. 8 is a flowchart for illustrating one mode of operation of a data server of the patient ID station.

FIG. 8 is a flow chart illustrating one mode of operation of data server 310. Data server 310 begins execution in step 450 and immediately proceeds to step 452 and waits for incoming messages from network interface 100. If there is a new message, data server 310 proceeds from step 454 to step 456 and determines the message type. Based on the message type, data server 310 branches to steps 460, 462 and 468 when the message is of unknown type, an acknowledgment or a request for patient information, respectively.

When the message received from network interface 100 contains a request of data, data server 310 reads the PSD file of information table 300 to find the patient associated with the ID code received from network interface 100. If the patient is found, data server 310 extracts from the PSD file all the patient data required for the construction of the DICOM file, as well as the general equipment data and the secondary equipment data which are stored in the GED and SED files, respectively. After that, data server 310 builds a response message in step 474, sends the response message to network interface 100 in step 476, and returns to step 452 for receiving subsequent messages.

When the message received from network interface 100 is an acknowledgment that a DICOM file has successfully been sent to PACS 60, data server 310 reads the PACS ACK file of information table 300 to find the patient associated with the ID code received from network interface 100. If the patient is found, data server 310 writes the acknowledgment of image sent in the corresponding field of the PACS ACK file in step 466 and returns to step 452 for receiving subsequent messages.

When the message is not recognized by data server 310 in step 458, or when data server 310 cannot find the patient in steps 470 and 464, data server 310 communicates an error message to the operator through visual interface 305 and requests operator intervention.

Print Server

The main function of print server 315 is to manage and server label imager 40. More specifically, print server 315 access information table 300 and facilitates the imaging of a label having a unique identifier on unexposed radiographic film. In one embodiment, the label is imaged directly on the radiographic film and is composed of four rows, each of 32 characters. The first row contains the hospital name, the second row contains the patient name and the birth date, the third row contains the current date and the hospital patient code, and the fourth row contains the current time, the film orientation code and the unique patient identifier.

Print server 315 is the server component of a client/server interface to label imager 40. When label imager 40 is initialized, it sends a message to print server 315 and requests the daily patient list. In response, print server 315 retrieves a list of unique identifiers for the patients from information table 300 and communicates the list to label imager 40. In one embodiment, label imager 40 includes a scroll display allowing the operator to view the list, select a current patient and image a label containing the corresponding patient information on the radiographic film. When label imager 40 images a label, it sends a message to print server 315. Print server 315 receives the message that the label has been imaged and sets a corresponding field in the ID ACK file.

In one embodiment, label imager 40 includes a bar code reader. In this embodiment, label imager 40 reads a bar code from the patient card, retrieves the patient information from the loaded daily patient list and images the patient information on the radiographic film. If, however, the read bar code information does not match any patients stored in the current patient list, label imager 40 sends a message to print server 315 containing the bar code information together with a data request. Based on the bar code information, which contains a unique patient identifier as printed by the bar code printer 70, print server 315 retrieves patient information from information table 300 or RIS interface 320 and communicates the information to label imager 40 to be imaged on the radiographic film label.

Figure 9:
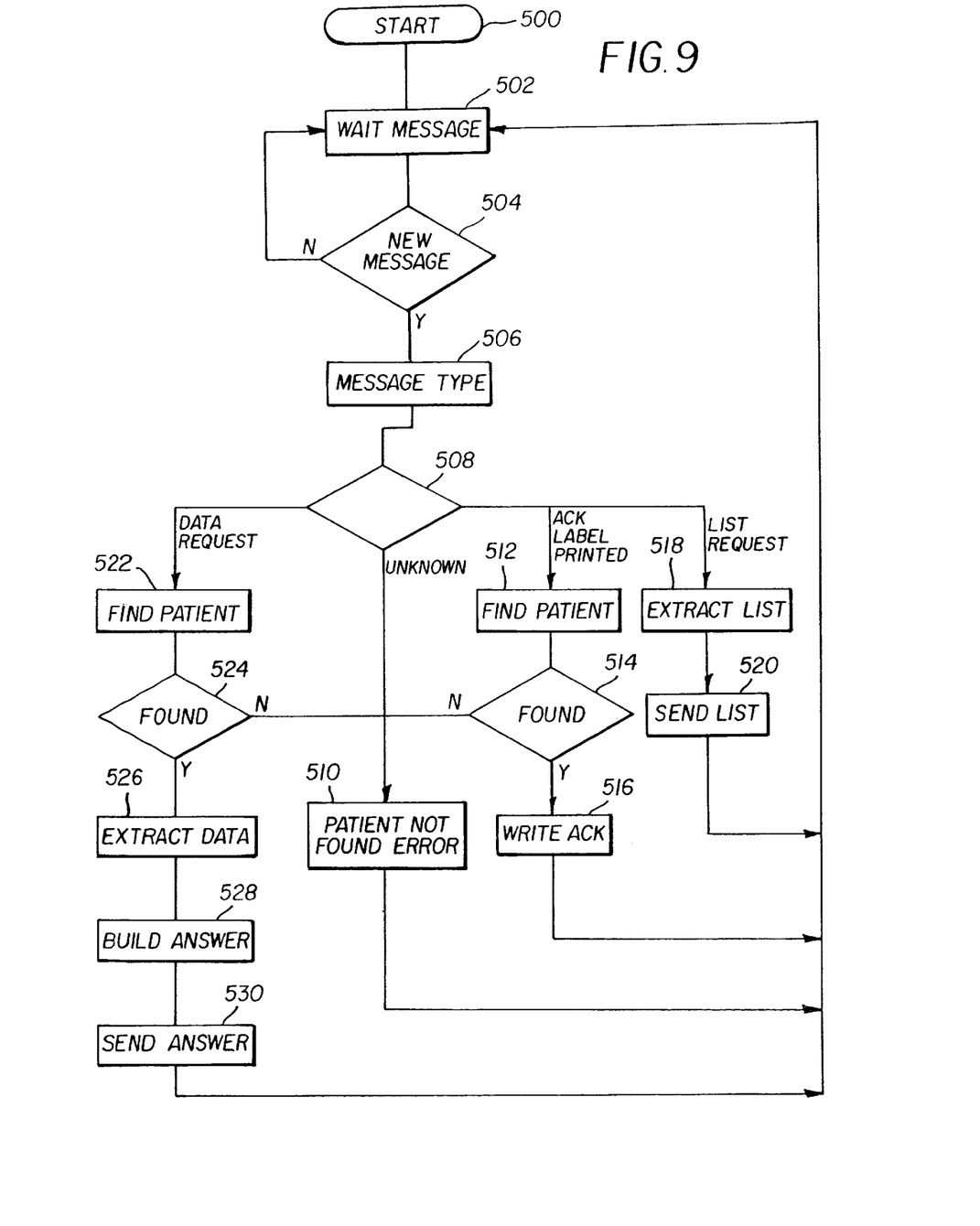
FIG. 9 is a flowchart for illustrating one mode of operation of a printer server of the patient ID station.

FIG. 9 is a flow chart illustrating one mode of operation of printer server 315. Printer server 315 begins execution in step 500 and immediately proceeds to step 502 and waits for incoming messages from label imager 40. If there is a new message, printer server 315 proceeds from step 504 to step 506 and determines the message type. Based on the message type, printer server 315 branches to steps 510, 512, 518 and 522 when the message is of unknown type, an acknowledgment, a request for daily patient list, or a request for patient information, respectively.

When the message received from label imager 40 contains the patient bar code together with a request of data, printer server 315 reads the PSD file of information table 300 to find the patient associated with the bar code received from label imager 40 (step 522). If the patient is found, in step 526 printer server 315 extracts from the PSD file the main generalities and ID code of the patient. After that, printer server 315 builds a response message in step 528, sends the response message to label imager 40 in step 530, and returns to step 502 for receiving subsequent messages.

When the message received from label imager 40 is the request of daily patient list, printer server 315 reads the PSD file of information table 300 and extracts from the PSD file the main generalities and ID code of all daily patients (step 518). After that, printer server 315 sends the response list to label imager 40 in step 520, and returns to step 502 for receiving subsequent messages.

When the message received from label imager 40 is an acknowledgment that a label has successfully been imaged on radiographic film by label imager 40, printer server 315 reads the ID ACK file of information table 300 to find the patient associated with the ID code received from label imager 40 (step 512). If the patient is found, printer server 315 writes the acknowledgment of label imaged in the corresponding field of the ID ACK file in step 516 and returns to step 502 for receiving subsequent messages.

When the message is not recognized by printer server 315 in step 508, or when printer server 315 cannot find the patient in steps 524 and 514, printer server 315 communicates an error message to the operator through visual interface 305 and requests operator intervention.

RIS Interface

The purpose of RIS interface 320 is to manage the communication with hospital's RIS 50 and to automatically create and update the daily list of patients to examine. RIS interface 320 contains the client component of a client/server interface, whose server runs on RIS 50. RIS interface 320 contacts the RIS and requests the list of the patients that are scheduled to be examined in a particular day. RIS interface 320 also periodically checks RIS 50 for updating the daily list. The updating procedure can also be activated by label imager 40 and/or by the operator through visual interface 305 when a patient is not found in the current list.

Figure 10:
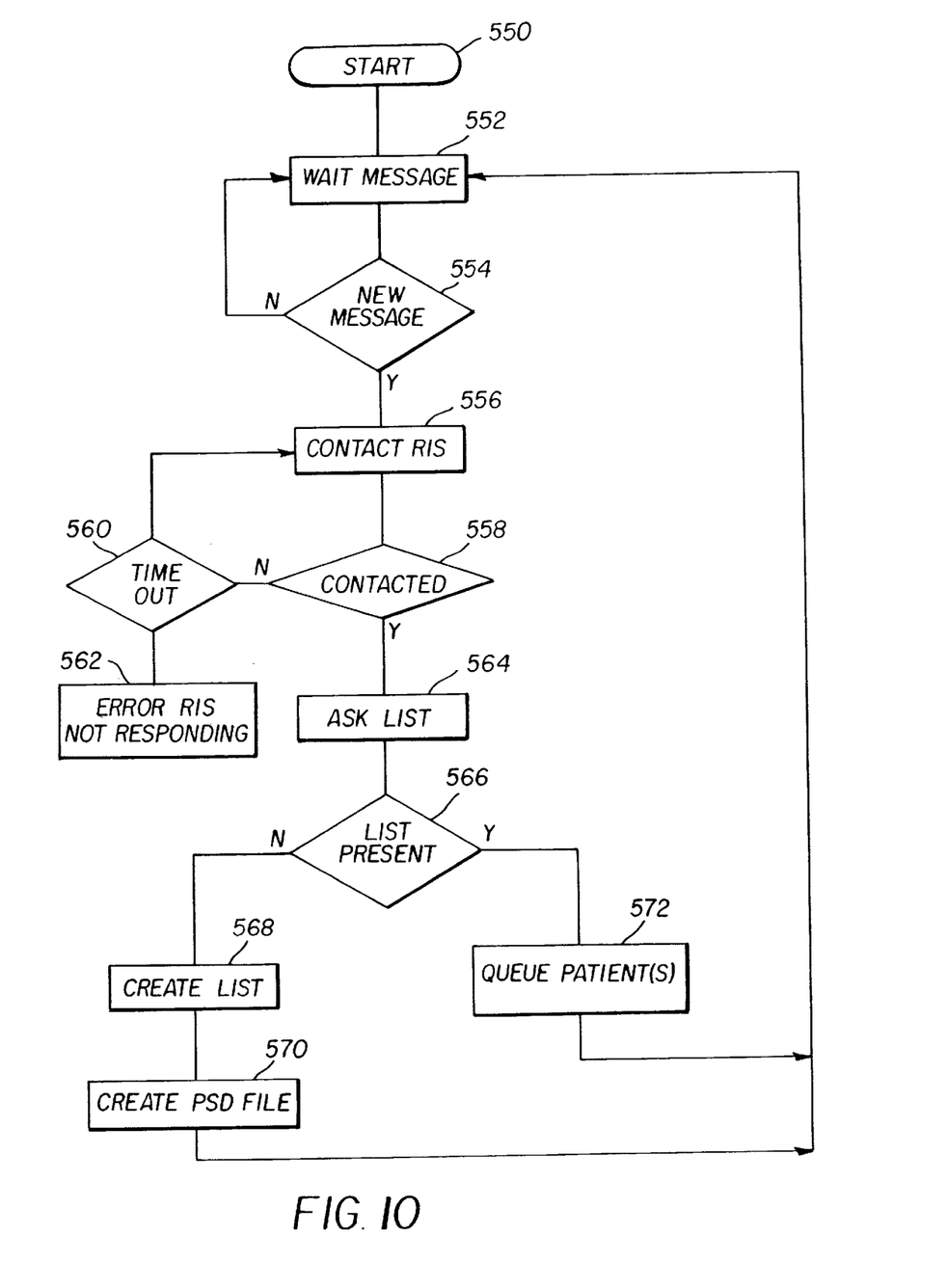
FIG. 10 is a flowchart for illustrating one mode of operation of a RIS interface of the patient ID station.

FIG. 10 is a flow chart illustrating one mode of operation of RIS interface 320. RIS interface 320 begins execution in step 550 and immediately proceeds to step 552 and waits for a message from visual interface 305 requesting the daily patient list. When the message is received, the RIS interface 320 contacts the RIS 50 in step 556. If the RIS 50 responds, the RIS interface 320 asks the daily list to the RIS 50 in step 564. If the RIS is not responding, a loop is started in step 560 until to time out, after that an error message signaling that the RIS 50 is not responding is sent to the visual interface 320 for operator intervention in step 562. Upon receiving the list from RIS 50, the RIS interface 320 reads the PSD file of the information table 300 and verifies if the daily patient list is already present. If so, the RIS interface 320 queues the additional patients in step 572; if not, the RIS interface 320 creates the list and writes it to the PSD file in step 568 and 570, respectively. After that, the RIS interface 320 returns to step 552 for receiving subsequent message.

Generating the DICOM File

As described in detail above, the present invention automatically associates medical images generated by an input imaging device 15 with the proper patient information. In one embodiment, the images and the associated patient information are associated and communicated to PACS according to the DICOM protocol. The information necessary to produce a DICOM file for communication can be subdivided in five categories: patient's data, hospital data, equipment data, image data and DICOM private data. Patient's data, hospital data, and equipment data are stored in information table 300 of the PIDS 110, as described above. Medical image data is produced by input imaging device 15 during digitization of the radiographic film and are managed by network interface 100. Private data is stored in the DICOM manager 130. The following tables summarize the content of each category, distinguishing between mandatory information (type 1), necessary information (type 2), and optional information (type 3). Absence of mandatory information is a protocol violation and produces an error, absence of necessary information can be supplied with 0 value or no value, while absence of optional information does not convey any significance and is not a protocol violation.

TABLE 4

Patient related information
PSD file

| Field | Attribute | Type |
|---|---|---|
| Patient | Patient's name | 2 |
|  | Patient ID | 2 |
|  | Patient's Birth Date | 2 |
|  | Patient's Sex | 2 |
|  | Referenced Patient Sequence | 3 |
|  | Other Patient ID* | 3* |
|  | Other Patient Names | 3 |
|  | Ethnic Group Patient Comments | 3 |
| Study | Referring Physician's Name | 2 |
|  | Study Description | 3 |
|  | Name of Physician reading study | 3 |
| Patient Study | Admitting Diagnosis Description | 3 |
|  | Patient's Age | 3 |
|  | Patient's Size | 3 |
|  | Patient's Weight | 3 |
|  | Occupation | 3 |
|  | Additional Patient's History | 3 |
| Series | Laterality | 2 |
|  | Body Part Examined | 3 |
| General Image | Patient orientation | 2 |

*The Other Patient ID attribute contains the ID code generated by visual interface 305. Even if this attribute is optional for the DICOM standard, it is necessary for the system of the present invention.

TABLE 5

General information
GED file

| Field | Attribute | Type |
|---|---|---|
| Series | Modality | 1 |
|  | Performing Physician's name | 3 |
|  | Operators' name | 3 |
|  | Protocol Name | 3 |
|  | Series Description | 3 |
| General Equipment (optional) | Manufactures | 2 |
|  | Institution name | 3 |
|  | Institution Address | 3 |
|  | Station Name | 3 |
|  | Institution Department Name | 3 |
|  | Manufacturer's Model Name | 3 |
|  | Device Serial Number | 3 |
|  | Software version | 3 |
|  | Spatial Resolution | 3 |
|  | Date of last calibration | 3 |
|  | Time of last calibration | 3 |
|  | Pixel Padding Value | 3 |

TABLE 6

Reserved information
SED file

| Field | Attribute | Type |
|---|---|---|
| SC Equipment | Conversion Type | 1 |
|  | Modality | 3 |
|  | SC Device ID | 3 |
|  | SC Device Manufacturer | 3 |
|  | SC Device Manufacturer's Model Name | 3 |
|  | SC Device Software Version | 3 |
|  | Digital Image Format Acquired | 3 |

TABLE 7

Image Information

| Field | Attribute | Type |
|---|---|---|
| Image Pixel | Samples per Pixel | 1 |
|  | Photometric Interpretation | 1 |
|  | Rows | 1 |
|  | Column | 1 |
|  | Bits allocated | 1 |
|  | Bits stored | 1 |
|  | High bit | 1 |
|  | Pixel Representation | 1 |
|  | Pixel Data | 1 |
|  | Smallest Image Pixel Value | 3 |
|  | Largest image Pixel Value | 3 |
| Series | Smallest Pixel Value in series | 3 |
|  | Largest Pixel value in series | 3 |

TABLE 8

DICOM private information

| Field | Attribute | Type |
|---|---|---|
| Study | Study Instance | 1 |
|  | Study Date | 2 |
|  | Study Time | 2 |
|  | Study ID | 2 |
|  | Accession Number | 2 |
|  | Referenced Study Sequence | 3 |
| Series | Series Instance UID | 1 |
|  | Series Number | 2 |
|  | Series Date | 3 |
|  | Series Time | 3 |
|  | Referenced Study Component Sequence | 3 |
| General Image | Image Number | 2 |
|  | Image Date | 2 |
|  | Image Time | 2 |
|  | Image Type | 3 |
|  | Acquisition Number | 3 |
|  | Acquisition date | 3 |
|  | Acquisition time | 3 |
|  | Referenced Image Sequence | 3 |
|  | Derivation Description | 3 |
|  | Images in acquisition | 3 |
|  | Image comments | 3 |
| SC Image | Date of secondary capture | 3 |
|  | Time of Secondary capture | 3 |
| SOP Common | SOP Class UID | 1 |
|  | SOP Instance UID | 1 |
|  | Specific Character Set | 1 |
|  | Instance Creation Date | 3 |
|  | Instance Creation Time | 3 |
|  | Instance Creator UID | 3 |

Various embodiments of a method and system for associating exposed radiographic film with proper patient information have been described. The invention maintains information for each patient to be examined in the current day and generates a unique identifier, such as a unique code, for each patient to be examined. The present invention images a label having one of the unique identifiers on each unexposed radiographic film before the film is used in imaging the patient via conventional x-ray techniques. After the film is exposed, the film is developed and digitized. Patient information is retrieved and associated with the digitized medical images by analyzing the digital image data in order to determine the unique identifier imaged on the radiographic film.

Several advantages of the present invention have been illustrated including ensuring the proper association of patient information with exposed radiographic film. Once properly associated, the digital image data and the patient information can be communicated to a Picture Archiving and Communication System. The present invention also allows for interfacing with a hospital's Radiology Information System, thus eliminating the need for manual entry of patient information. This application is intended to cover any adaptations or variations of the present invention. It is manifestly intended that this invention be limited only by the claims and equivalents thereof.

We claim:

1. A system for associating a radiographic film with patient information comprising:
    an imager for imaging a label having a unique patient identifier on a radiographic film;
    an input imaging device including:
        a processor for developing the radiographic film having the label imaged thereon, thereby forming at least one visible medical image on the radiographic film, and
        a film digitizer coupled to the processor for digitizing the medical image and the label image, thereby producing digital image data; and
    an interface device for analyzing the digital image data to determine the patient identifier of the label and associating the digitized radiographic film with one of a plurality of patients based on the determined patient identifier;
    wherein the interface device stores patient information in an information table having a plurality of entries such that each entry of the information table has a unique identifier, wherein the interface device selects one of the entries of information table when the unique identifier of the selected entry corresponds to the unique patient identifier of the label.

2. The system of claim 1, wherein the interface device analyzes the digital image data by performing optical character recognition techniques on the digital image data to determine the patient identifier of the label.

3. The system of claim 1, wherein the interface device further comprises:
    a patient identification station managing the information table including retrieving patient information from the selected entry; and
    a network interface for receiving the digital image data from the input imaging device and communicating the patient identifier to the patient identification station, wherein the patient identification station communicates patient information from the selected entry to the network interface.

4. The system of claim 3, wherein the network interface communicates the digital image data and the patient information received from the patient identification system to a Picture Archiving and Communicating System.

5. The system of claim 4, wherein the patient identification station communicates the patient information to the network interface in compliance with the DICOM standard.

6. The system of in the network interface includes a DICOM manager for building a DICOM file containing the digital image data and the patient information received from the patient identification system, wherein the network interface communicates the DICOM file to the Picture Archiving and Communicating System.

7. The system of claim 3, wherein the patient identification station updates the information table by retrieving current patient information from a radiology information system.

8. The system of claim 3, wherein the patient identification station includes a visual interface for providing a visual display to allow an operator to modify the patient information of the information table.

9. The system of claim 8, wherein the network interface includes a failure manager for generating an error message when the network interface is unable to determine the patient identifier of the label from the digital image data, and further wherein the failure manager communicates the error message to the visual interface to allow the operator to enter patient information for the developed radiographic film.

10. The system of claim 3, wherein the patient identification station includes a print server for retrieving at least one unique identifier of the entries of the information table and communicating the retrieved unique identifier to the label imager for imaging as the patient identifier on the radiographic film.

11. The system of claim 3, wherein the patient identification station is a software module executing on a first computer and the network interface is a software module executing on a second computer.

12. The method of claim 11, wherein the selecting step includes the steps of:
    retrieving patient information from the selected entry; and
    communicating the digital image data and the retrieved patient information to a Picture Archiving and Communicating System.

13. The method of claim 12, wherein the communicating step communicates the digital image data and the retrieved patient information in compliance with the DICOM standard.

14. The method of claim 13, wherein the communicating step building a DICOM file contains the digital image data and the patient information received from the patient identification system.

15. The method of claim 11, wherein the storing step includes the step of retrieving current patient information from a radiology information system.

16. The method of claim 11, wherein the storing step includes the step of providing a visual display to allow an operator to modify the patient information of the information table.

17. The method of claim 16, wherein the providing step includes the step of displaying an error message when the analyzing step is unable to determine the patient identifier of the label from the digital image data to allow the operator to enter patient information for the developed radiographic film.

18. The method of claim 17, wherein the printing step includes the step of retrieving a bar-code representing the patient identifier on a patient card.

19. The method of claim 11, wherein the imaging step includes the step of retrieving at least one unique identifier of the entries of the information table and communicating the retrieved unique identifier to a imager for imaging as the patient identifier of the label.

20. The system of claim 1, wherein the system further comprises a bar-code printer to form a bar-code on a patient card in order to represent the patient identifier.

21. A method for associating a radiographic film with one of a plurality of patients comprising the steps of:

imaging a label having a patient identifier on a radiographic film;

developing the radiographic film having the label imaged thereon to form at least one visible medical image on the radiographic film;

digitizing the medical image and the label image to produce digital image data;

analyzing the digital image data to determine the patient identifier of the label imaged on the radiographic film; and     associating the developed radiographic film with one of the patients as a function of the determined patient identifier;

wherein the associating step comprises the steps of:

storing patient information in an information table having a plurality of entries such that each entry of the information table has a unique identifier; and         selecting one of the entries of information table when the unique identifier of the selected entry corresponds to the patient identifier of the label.

22. The method of claim 21, wherein the analyzing step performs optical character recognition techniques on the digital image data to determine the patient identifier of the label.

* * * * *